Figure 1:
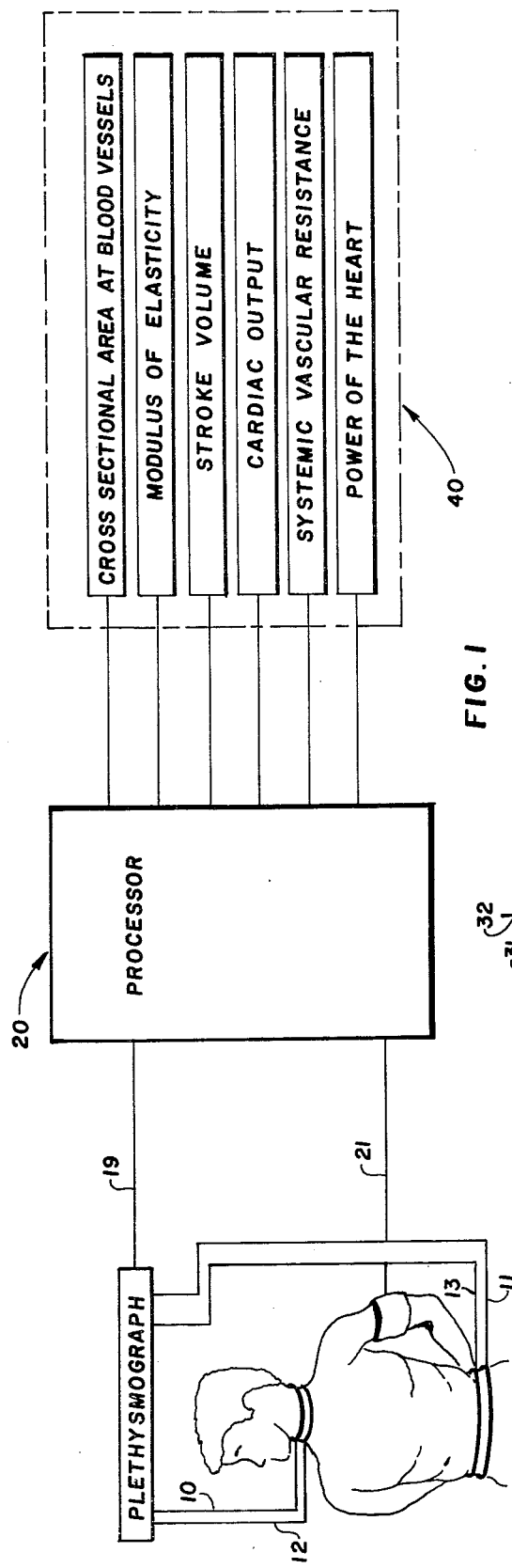

United States Patent [19]

Djordjevich et al.

[11] 4,437,469
[45] Mar. 20, 1984

[54] SYSTEM FOR DETERMINING CHARACTERISTICS OF BLOOD FLOW

[75] Inventors: Ljubomir Djordjevich, Chicago; Max S. Sadove, River Forest, both of Ill.

[73] Assignee: Rush-Presbyterian-St. Luke's Medical Center, Chicago, Ill.

[21] Appl. No.: 191,387

[22] Filed: Sep. 29, 1980

[51] Int. Cl.³ .................................................. A61B 5/02
[52] U.S. Cl. ..................................... 128/672; 128/677; 128/693; 128/713; 128/734
[58] Field of Search ............... 128/693, 734, 691, 694, 128/677, 713, 672, 670, 671

[56] References Cited

U.S. PATENT DOCUMENTS 3,734,086  5/1973  Phelps .................................. 128/691
3,920,004  11/1975  Nakayama ...................... 128/691 X
3,996,925  12/1976  Djordjevich ........................ 128/693
4,144,878  3/1979  Wheeler .............................. 128/693

Primary Examiner—Kyle L. Howell
Assistant Examiner—John C. Hanley
Attorney, Agent, or Firm—Fitch, Even, Tabin & Flannery

[57] ABSTRACT

A method and apparatus for determining and displaying hemodynamic characteristics of a living body instantaneously and over a time period, i.e., rate of blood flow, stroke volume, cardiac output, cardiac index, systemic vascular resistance, useful power of the heart and elastic properties of the walls of blood vessels. The improved method and apparatus deal with physical measurements of body electrical impedance and blood pressure in relationship with other known or derived factors to produce signals representing these characteristics and which may be displayed for the information of surgeons or others who may be interested in this information.

28 Claims, 2 Drawing Figures

SYSTEM FOR DETERMINING CHARACTERISTICS OF BLOOD FLOW

This invention relates to a process and apparatus for monitoring the flow of blood in a section of a living body. More particularly, the invention relates to a process and apparatus in which an electrical signal representing the electrical impedance of the section and also an electrical signal representing blood pressure are produced and each passed through electrical units to produce signals describing characteristics relating to the flow of blood through the section.

BACKGROUND

Methods which have been devised for determining blood flow characteristics include indicator dilution methods, magnetic flow meters, ultrasonic blood flow meters, impedance cardiography blood flow determination by radiographic methods and by a method which is known as the Fick Method.

These methods have proved to be inadequate to meet the needs of surgeons and others in medical practice at the present time.

My U.S. Pat. No. 3,996,925 describes a system for determining blood flow using electrical impedance across a section of a living body, and some of the characteristics of blood flow may be determined by this system with a fair degree of accuracy, but there is a long-standing need for a system which is more accurate and which is effective for determining many other characteristics of flood flow and which is sensitive to the variation of individual persons or sections of the body under test. For example, in the determination of rate of blood flow, it has been necessary to utilize a fixed or an average value as the modulus of elasticity (E) for the walls of blood vessels. It would, indeed, be desirable to known and to use a value for this modulus which is determined at the time as a result of sensing indications of the particular individual under test. Also, it would be very desirable to determine other characteristics such as cross-sectional area of the blood vessels and the variations of this area over a selected time period or during the cycle of blood flow, or at any particular times during the cycle.

Accordingly, I have set about to discover methods and means for accurately determining and displaying, or otherwise demonstrating, information as it is being produced about many blood flow characteristics, some of which have never before been demonstrted, at any instant of time, and to demonstrate the variation of such characteristics during a cycle, during any particular part of a cycle, or during any selected time period. Another of my objectives was to utilize additional indications obtained from the body under test and to eliminate the use of average or general constants as much as possible in making the determinations.

SUMMARY

In my improved system the determining and demonstrating of cardiovascular characteristics, I measured the electrical impedance across a section of the living body to obtain an electrical signal representative of electrical impedance, measured the blood pressure of this body to obtain an electrical signal having a value representative of blood pressure in the body, and utilized these two electrical signals in determining characteristics of blood flow in this section.

DESCRIPTION OF INVENTION

Figure 2:
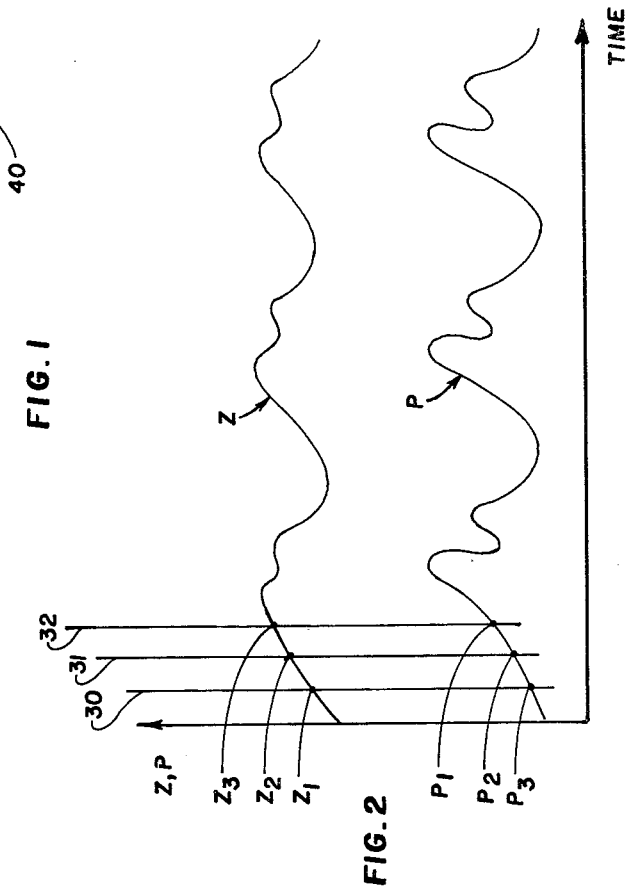

An embodiment of the invention is illustrated in the accompanying drawing in which:

FIG. 1 is a schematic diagram of apparatus utilized in carrying out the improved method, and FIG. 2 is a graph illustrating typical curves describing values of electrical signals representing impedance and blood pressure.

As illustrated, a plethysmograph is employed which may be similar to that referred to in my U.S. Pat. No. 3,996,925 or to that described in the Kubicek et al. U.S. Pat. No. 3,340,867. In this arrangement, there is an outer pair of electrodes, one of which is affixed to the patient's neck and the other of which is affixed to the patient's waist, and an oscillating current is passed between these electrodes. A second pair of electrodes is likewise affixed between the first pair of electrodes for the purpose of measuring electrical impedance.

I may utilize an impedance plethysmograph for producing an electrical signal representing electrical impedance. The electrical impedance signal produced by the plethysmograph is delivered to the processor 20 through the connection which is designated 19.

Referring again to the drawing, a very important feature of this invention is the inclusion of a device here shown as having a band extending about the upper arm of the patient. I may use a device which, in itself, yields an electrical signal representing blood pressure, and the output of such a device may be connected directly through connection 21 to the processor 20; or I may use a device which yields a measurement of the pressure on a scale of any kind, and this result may be converted to an electrical signal which is fed into the processor.

For purposes of illustration, there is shown in FIG. 2 a curve Z representing electrical impedance across a section of a living body over a certain time period, such as three or four cardiac cycles, and another curve P representing blood pressure. For example, the point $Z_1$ on the impedance curve shows the value of the impedance at a selected time or point in the cycle, and point $P_1$ shows the blood pressure at this same time or point in the cycle. Likewise, the point $Z_2$ shows the impedance at a little later time or point in the cardiac cycle while point $P_2$ shows the corresponding blood pressure at this later time or point in the cycle; and the point $Z_3$ shows the impedance at a still later point in the cycle, and point $P_3$ shows the value of corresponding blood pressure at this later time or point in the cycle of blood flow. The vertical lines 30, 31, and 32, joining the points of equal time, show that these measurements of impedance and blood pressure measurements are taken simultaneously, and the curve indicates continuity of the measurements.

The processor 20 may contain electronic processing units, each capable of modifying the impedance or blood pressure signals by addition, subtraction multiplication, division, differentiation, integration or exponentiation. The processor is constructed to simulate the set of formulae which are selected to determine (from the impedance signals and blood pressure signals) the values of the different characteristics of blood flow. Thus, both the electrical signal representing impedance and the electrical signal representing blood pressure are utilized in the determination of the values of these characteristics and in the display or demonstration of these characteristics.

The processor may contain electronic units for performing the prescribed functions as above explained or may be in the form of a microprocessor which is programmed to perform the prescribed mathematical manipulations.

To demonstrate the use of the improved system for making determination of blood flow characteristics and the display of the values of these characteristics, I will take specific examples and show the progression of specific operations of the system.

Let us take the characters $Z_1$, $Z_2$, and $Z_3$ to represent values of impedance at three successive time positions on curve Z and $P_1$, $P_2$, and $P_3$ to represent values at corresponding time positions on curve P.

It is possible to measure the applicable modulus of elasticity of the blood vessel walls.

Based on principles of electricity, the cross-sectional area, a, of blood vessels in a section of a living body:

$$a = \left(\frac{1}{Z} - \frac{1}{Z_c}\right) \rho L \quad \text{(Formula No. 1)}$$

where
Z is the total electrical impedance which combines the impedance of the blood volume and the other tissues.
$Z_c$ is the impedance of the tissues.
$\rho$ is the resistivity of blood, (typically 200 ohm-centimeters).
L is the distance between the inner electrodes which are used to measure Z. The value of L is measured when the electrodes have been positioned on the patient.

Based on principles of mechanics, the cross section of area, a, may be calculated as $$a = a_o \left(\frac{P}{E} + 1\right)^2 \quad \text{(Formula No. 2)}$$

where $a_o$ is the area of the unstretched blood vessels, P is blood pressure, and E is a quantity representing modulus of elasticity of the walls of the blood vessels.

Z is measured, continuously or discretely, as by an impedance plethysmograph, or by impedance cardiograph, and P is measured by a blood pressure measuring device and $$\left(\frac{1}{Z} - \frac{1}{Z_c}\right) \rho L = a_o \left(\frac{P}{E} + 1\right)^2. \quad \text{(Formula No. 3)}$$

The processor is utilized to determine the values of $Z_c$, $a_o$ and E from the pairs of simultaneously measured values of Z and P which are successively plugged into the circuits representing Formula No. 3.

Thus, if three corresponding values are $Z_1$ and $P_1$, $Z_2$ and $P_2$, $Z_3$ and $P_3$, the corresponding forms of Formula No. 3 will be $$\left(\frac{1}{Z_1} - \frac{1}{Z_c}\right) \rho L = a_o \left(\frac{P_1}{E} + 1\right)^2 \quad \text{(Formula No. 4)}$$

$$\left(\frac{1}{Z_2} - \frac{1}{Z_c}\right) \rho L = a_o \left(\frac{P_2}{E} + 1\right)^2 \quad \text{(Formula No. 5)}$$

$$\left(\frac{1}{Z_3} - \frac{1}{Z_c}\right) \rho L = a_o \left(\frac{P_3}{E} + 1\right)^2 \quad \text{(Formula No. 6)}$$

and the values of $a_o$, $Z_c$ and E are uniquely determined. Values of $\rho$ and L were previously known.

The value of E may first be determined as follows:
From the measured values of $Z_1$, $Z_2$ and $Z_3$ the value of N is $$N = \frac{Z_1 - Z_3}{Z_1 - Z_2} \cdot \frac{Z_2}{Z_3} \quad \text{(Formula No. 7)}$$

From this, the value of E is found from the determined value of N, and the values of $P_1$, $P_2$ and $P_3$ which are measured simultaneously with $Z_1$, $Z_2$ and $Z_3$ respectively $$E = 1 \cdot \frac{P_1^2 - P_3^2 + N(P_3^2 - P_2^2)}{P_3 - P_1 + N(P_2 - P_3)} \quad \text{(Formula No. 8)}$$

The values of $a_o$ and $Z_c$ are then found so that $$a_o = \frac{\rho L \left(\frac{1}{Z_1} - \frac{1}{Z_2}\right)}{\left(\frac{P_1}{E} + 1\right)^2 - \left(\frac{P_2}{E} + 1\right)} \quad \text{(Formula No. 9)}$$

The value of $\rho$ is obtained from the blood sample of the patient, or by assuming a typical value of $\rho = 200$ ohm-cm. The value of L is obtained by measuring the shortest distance between the inner electrodes of the plethysmograph. Both the values of $\rho$ and L are fed into the processor by the operator, and $$\frac{1}{Z_c} = \frac{1}{Z_1} - \frac{a_o}{\rho L}\left(\frac{P_1}{E} + 1\right)^2 \quad \text{(Formula No. 10)}$$

When E, $a_o$ and $Z_c$ are determined, then the value of the cross-sectional area, a, at any instant of time can be obtained and displayed on the display device 40. This display may be digital or in the form of a curve which is changing with time. This value is obtained by the use of either Formula No. 1 or Formula No. 2, these formulae being represented by electronic circuits in the processor 20.

The instantaneous flow of blood through blood vessels of cross-sectional area, a, is found from $$Q = \frac{a^2 \cdot p}{8\pi L \eta} \quad \text{(Formula No. 11)}$$

where $\eta$ is dynamic viscosity of blood previously determined, and p is the average blood pressure drop along the blood vessel; also measured beforehand, or obtained from the following formula $$p = \frac{C}{\sigma(a_{max} + a_{min})} \quad \text{(Formula No. 12)}$$

where $$C = 0.25126 \sqrt{E} \quad \text{(Formula No. 13)}$$

and $$\sigma = \frac{1}{8\pi\nu} \quad \text{(Formula No. 14)}$$

where $\nu$ is kinematic viscosity of blood measured beforehand, $a_{min}$ and $a_{max}$ are respectively the smallest and largest values of a as measured during the cardiac cycle.

The values of $\eta$ and $\nu$ are either measured from the blood sample of the patient, or by assuming respective typical values. These values are fed into the processor by the operator.

The cardiac output, CO, may now be obtained by integrating Q over a one-minute period according to the following formula:

$$CO = \int_0^{1 \text{ min}} Q dt \quad \text{(Formula No. 15)}$$

Stroke volume, SV, is obtained by the following equation:

$$SV = \frac{CO}{\text{pulse rate}} \quad \text{(Formula No. 16)}$$

where pulse rate is measured on the patient, and entering into the processor by the operator, or directly from the pulse rate measuring device.

Systemic vascular resistance, SVR, is obtained as follows:

$$SVR = \frac{80000}{60 \cdot CO} \int_0^{60 \text{ sec}} (P - 4) dt \quad \text{(Formula No. 17)}$$

Useful power of the heart, POW, is obtained by the equation $$POW = \frac{POWP + POWK}{10,000,000} \quad \text{(Formula No. 20)}$$

where $$POWP = \frac{1332}{60} \int_0^{60 \text{ sec}} Q(P - 4) dt \quad \text{(Formula No. 19)}$$

and $$POWK = \frac{0.529}{60} \int_0^{60 \text{ sec}} \frac{Q^3}{a^2} \quad \text{(Formula No. 18)}$$

Alternately, instead of determining E by use of Formula No. 8, the following formula is applicable:

$$E = B \times R \quad \text{(Formula No. 21)}$$

where $$B = \frac{P_1 - P_3}{\sqrt{M} - 1} \quad \text{(Formula No. 22)}$$

and $$M = \frac{Z_2 - Z_3}{Z_2 - Z_1} \cdot \frac{Z_1}{Z_3} \quad \text{(Formula No. 23)}$$

and $$R = D + F \cdot Z_2 \quad \text{(Formula No. 24)}$$

and D and F are constant numbers, experimentally determined to have values $D = 0.7254456$, $F = 0.00458779$.

The remainder of the exercise follows the same path as previously outlined from Formula No. 9.

In each of the above demonstrations I measure impedance by contact with a living body and obtain an electrical signal which represents impedance of that living individual body; and also, I measure blood pressure by contact with this same living body and obtain an electrical signal which represents blood pressure within this same body, both of these signals being taken simultaneously so that the value of the signal representing impedance at any instant, over any time period it may be taken, will have a corresponding value of blood pressure which is reflected in the signal representing blood pressure. These signals representing corresponding values of impedance and blood pressure are essential and when placed in the formulae setting forth their relationship with known constants and other derived factors, result in values and variations representing the characteristics useful in surgery or in other medical treatment of patients. It is of great value to a surgeon, for example, to glance up at the display apparatus and note, for example, changing rate of blood flow, the changing values of elasticity in the walls of the arteries, and the change in the power of the heart action. Such characteristics may be illustrated in curves which are displayed on a screen or which may be by digits displayed in a digital indicator.

In the construction of the improved system, formulae must be selected which utilize values of impedance and blood pressure and which result in the value of the desired blood flow characteristics such as rate of flow or modulus of elasticity, and the processor 20 is constructed so as to connect the units of the processor in an order and in a relationship to manipulate the measured blood pressure and impedance signals in accordance with these formulae, and the display apparatus must be connected and arranged to be responsive to the signals coming from the processor and for the display of values corresponding to these resulting signals coming from the processor.

One or several channels may be set up in the processor. For example, one channel may result in a signal which represents rate of flow, another may result in a signal representing area of blood vessels, etc. The signals from each of these channels will have incorporated therein, in some way, the values of impedance and blood pressure or derivatives thereof, and will be the result of mathematical manipulations as directed by the selected formulae so that the blood characteristics for which the formulae were selected are shown separately in the display.

What I claim is:

1. A method for measuring a blood circulation characteristic comprising measuring electrical impedance across a section of a living body having an unobstructed blood flow, simultaneously with said measurement of electrical impedance measuring blood pressure in said body, and passing the values of impedance measurement and also the values of blood pressure measurement, each in the form of an electrical signal, through a processor and determining from the electrical impedance and blood pressure signals electrical signals representing said blood circulation characteristic.

2. A method as set forth in claim 1 including the step of displaying the value of said signal representative of the selected characteristic.

3. A method as set forth in claim 1 wherein the step of determining said blood circulation characteristic includes the step of determining the modulus of elasticity of the arterial walls in said body section.

4. Apparatus for determining the value of a characteristic of blood circulation comprising a plethysmograph connected to a living body to measure unobstructed blood flow and which has electrodes spaced by a section of said body, a processor, said plethysmograph having its output connected to said processor and being capable of delivering through its connection to said processor an electric signal representing electrical impedance of said body section, a device for measuring blood pressure of said body having its output connected to said processor and which is capable of delivering through its connection to said processor an electric signal representative of the measured blood pressure, said processor having therein electronic units for determining a blood circulation characteristic.

5. Apparatus as set forth in claim 4 including means for displaying the value of said blood circulation characteristic.

6. Apparatus as set forth in claim 4 in which said blood circulation characteristic is cardiac output.

7. Apparatus as set forth in claim 4 in which said blood circulation characteristic is rate of flow.

8. Apparatus as set forth in claim 4 in which said blood circulation characteristic is modulus of elasticity of the walls of blood vessels within said body section.

9. A method for determining a cardiac output, stroke volume, power of heart, or other cardiac characteristic comprising measuring electrical impedance across a section of a living body having an unobstructed volume flow of blood, simultaneously with said measurement of electrical impedance, measuring blood pressure in said body, and passing the values of impedance measurement and also the values of blood pressure measurement, each in the form of an electrical signal, through a processor, and determining from the electrical signals a cardiac circulation characteristic.

10. A method for measuring a blood flow characteristic comprising measuring electrical impedance across a section of a living body at three time positions, simultaneously with said measurement of electrical impedance measuring blood pressure in said body at said time positions, and passing the values of the impedance measurements and also the values of blood pressure measurements, each in the form of electrical signals, through a processor and determining from the electrical impedance and blood pressure signals electrical signals representing said blood flow characteristic.

11. A method for measuring a blood circulation characteristic comprising measuring electrical impedance across a section of a living body, simultaneously with said measurement of electrical impedance measuring blood pressure at a location in said body non contiguous to the electrical impedance measuring, and passing the values of impedance measurement and also the values of blood pressure measurement, each in the form of an electrical signal, through a processor and determining from the electrical impedance and blood pressure signals electrical signals representing said blood circulation characteristic.

12. A method for measuring a cardiac blood flow characteristic comprising measuring electrical impedance across a section of a living body, simultaneously with said measurement of electrical impedance non-occlusively measuring blood pressure in said body, and passing the values of impedance measurement and also the values of blood pressure measurement, each in the form of an electrical signal, through a processor which has been constructed and arranged to simultaneously coorelate a predefined plurality of simultaneous measurement pairs of said electrical impedance blood pressure signals, to obtain an electrical signal representing said cardiac blood flow characteristic.

13. A method for measuring a blood flow characteristic comprising measuring electrical impedance across the thoracic section of a living body, simultaneously with said measurement of electrical impedance measuring blood pressure in said body, and passing the values of impedance measurement and also the values of blood pressure measurement, each in the form of an electrical signal, through a processor, and, determining from the electrical impedance and blood pressure signals electrical signals representing said blood flow characteristic.

14. Apparatus for determining the value of cardiac output, stroke volume, power of the heart, or other cardiac characteristic of blood flow comprising a plethysmograph connected to a living body and which has electrodes spaced by a section of said body, a processor, said plethysmograph having its output connected to said processor and being capable of delivering through its connection to said processor an electrical signal representing electrical impedance of said body section, a device for measuring blood pressure of said body having its output connected to said processor and which is capable of delivering through its connection to said processor an electrical signal representative of the measured blood pressure, said processor having therein electronic units for determining said cardiac blood flow characteristic.

15. Apparatus for determining the value of a characteristic of blood flow comprising a plethysmograph connected to a living body and which has electrodes spaced by a section of said body, a processor, said plethysmograph having its output connected to said processor and being capable of delivering through its connection to said processor an electrical signal representing electrical impedance of said body section, a device for non-occlusively measuring blood pressure of said body having its output connected to said processor and which is capable of delivering through its connection to said processor an electrical signal representative of the measured blood pressure, said processor determining said characteristic of blood flow responsive to three simultaneous sets of impedance and blood pressure measurement signals.

16. Apparatus for determining the value of a characteristic of blood flow comprising: a plethysmograph connected to a living body and which has electrodes spaced by a section of said body, a processor, said plethysmograph having its output connected to said processor and being capable of delivering through its connection to said processor an electrical signal representing electrical impedance of said body section, a device for measuring blood pressure at a location in said body non contiguous to the electrical impedance measuring, having its output connected to said processor and which is capable of delivering through its connection to said processor an electrical signal representative of the measured blood pressure, said processor determining from the impedance and blood pressure signals, said blood flow characteristic.

17. Apparatus for determining the value of a characteristic of blood flow comprising a plethysmograph connected to a living body and which has electrodes spaced by a section of said body, a processor, said plethysmograph having its output connected to said processor and being capable of delivering through its connection to said processor an electrical signal representing electrical impedance of said body section, a device for measuring blood pressure without blocking blood flow of said body having its output connected to said processor and which is capable of delivering through its connection to said processor an electrical signal representative of the measured blood pressure, said processor for determining from the impedance and blood pressure signals, said blood flow characteristic.

18. The apparatus as in claim 15 or 16 further characterized in that said plethysmograph electrodes are spaced across the thoracic section of said body.

19. Apparatus as set forth in claim 15 or 16 in which said characteristic is cardiac output.

20. Apparatus as set forth in claim 14 or 15 or 16 in which said characteristic is rate of flow.

21. Apparatus as set forth in claim 14 or 15 or 16 in which said characteristic is modulus of elasticity of the walls of blood vessels within said body section.

22. A method for determining cardiac blood flow characteristics comprising:
measuring electrical impedance across a first region of a living body while simultaneously measuring blood pressure at a section region of said body non-contiguous to said first region,
processing said measured electrical impedance and blood pressure measurements to determine said cardiac blood flow characteristics.

23. The method as in claim 22 wherein said first region is the thoracic region.

24. The method as in claim 22 wherein said second region is a body limb.

25. A system for determining blood flow characteristics of a living body comprising:
first means for noninvasively measuring blood vessel cross-sectional area in a section of said body;
second means for measuring blood pressure in said body simultaneously with said measurement of said first means,
processor means for determining said blood flow characteristics responsive to said first and second means.

26. The system as in claim 25 wherein said first means is further comprised of:
means for measuring electrical impedance across the thoracic region of said body,
means for measuring blood pressure, simultaneous to said impedance measurement, at a second region of said body non-contiguous to said thoracic region, and
means for determining the cardiac blood flow characteristic responsive to said measured electrical impedance and blood pressure.

27. A system for determining hemodynamic characteristic comprising:
means for measuring electrical impedance across a first region of said body,
means for measuring blood pressure, simultaneous to said impedance measurement, at a second region of said body non-contiguous to said first region, and
means for determining the hemodynamic characteristic responsive to said measured electrical impedance and blood pressure.

28. The system as in claim 27 wherein said second region is an arm of the body.

* * * * *

UNITED STATES PATENT AND TRADEMARK OFFICE
CERTIFICATE OF CORRECTION

PATENT NO. : 4,437,469
DATED : March 20, 1984
INVENTOR(S) : Djordjevich et al.

It is certified that error appears in the above-identified patent and that said Letters Patent is hereby corrected as shown below:

Column 1, line 19 after "Cardiography" insert a comma (,).

Column 1, line 32 "flood" should read --blood--.

Column 1, line 38 "known" should read --know--.

Column 1, line 50 "demonstrted" should read --demonstrated--.

Column 2, line 58 after "subtraction" insert a comma (,).

Column 9, line 40 "section" should read --second--.

Signed and Sealed this

Sixteenth Day of October 1984

[SEAL]

Attest:

GERALD J. MOSSINGHOFF

Attesting Officer

Commissioner of Patents and Trademarks